United States Patent [19]
Bal-Tembe et al.

[11] Patent Number: 5,821,252
[45] Date of Patent: Oct. 13, 1998

[54] METHOD OF BLOCKING NERVE CONDUCTION BY TREATMENT WITH BRANCHED-CHAIN ESTERS OF 2-[4-(2-PIPERIDINE-ETHOXY)-BENZOYL]-BENZOIC ACID AND PHARMACEUTICALLY ACCEPTABLE SALTS THEREOF

[75] Inventors: Swati Bal-Tembe; Jürgen Blumbach, both of Bombay; Alihussein Nomanbhai Dohadwalla, deceased, late of Bombay, by Rashida Alihussein Dohadwalla, legal representative; Bansi Lal, Bombay; Narayan Sudhindra Punekar, Belgaum; Ramanujam Rajgopalan, Bombay, all of India; Richard Helmut Rupp, Königstein/Taunus; Martin Bickel, Bad Homburg, both of Germany

[73] Assignee: Hoechst Aktiengesellschaft, Frankfurt am Main, Germany

[21] Appl. No.: 474,550

[22] Filed: Jun. 7, 1995

Related U.S. Application Data

[63] Continuation-in-part of Ser. No. 232,436, Apr. 21, 1994, abandoned, which is a continuation of Ser. No. 995,524, Dec. 23, 1992, abandoned, which is a continuation of Ser. No. 424,338, Oct. 19, 1989, abandoned.

[30] Foreign Application Priority Data

Oct. 21, 1988 [EP] European Pat. Off. .............. 88117521

[51] Int. Cl.$^6$ ....................... A61K 31/445; C07D 211/34
[52] U.S. Cl. ............................................ 514/317; 546/239
[58] Field of Search ............................... 514/317; 546/239

[56] References Cited

U.S. PATENT DOCUMENTS

| | | | |
|---|---|---|---|
| 2,681,340 | 6/1954 | Ehrhart et al. | 546/239 |
| 4,233,298 | 11/1980 | Mieville | 424/244 |
| 4,294,841 | 10/1981 | Champseix et al. | 424/267 |

FOREIGN PATENT DOCUMENTS

| | | | |
|---|---|---|---|
| 0364941 | 4/1990 | European Pat. Off. | 546/239 |
| A-1 057 372 | 3/1954 | France | 546/239 |
| 0896945 | 11/1953 | Germany | 546/239 |

OTHER PUBLICATIONS

Langle et al, Exp. Toxic Pathol., vol. 45, pp. 473–479 (1993/1994).

*Primary Examiner*—Floyd D. Higel
*Attorney, Agent, or Firm*—Finnegan, Henderson, Farabow, Garrett & Dunner, L.L.P.

[57] ABSTRACT

Compounds of the formula III

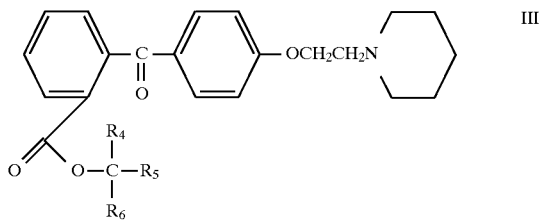

in which $R_4$ and $R_5$ are $CH_3$ amd $R_6$ is hydrogen, have prolonged spasmolytic and anaesthetic activity.

2 Claims, 3 Drawing Sheets

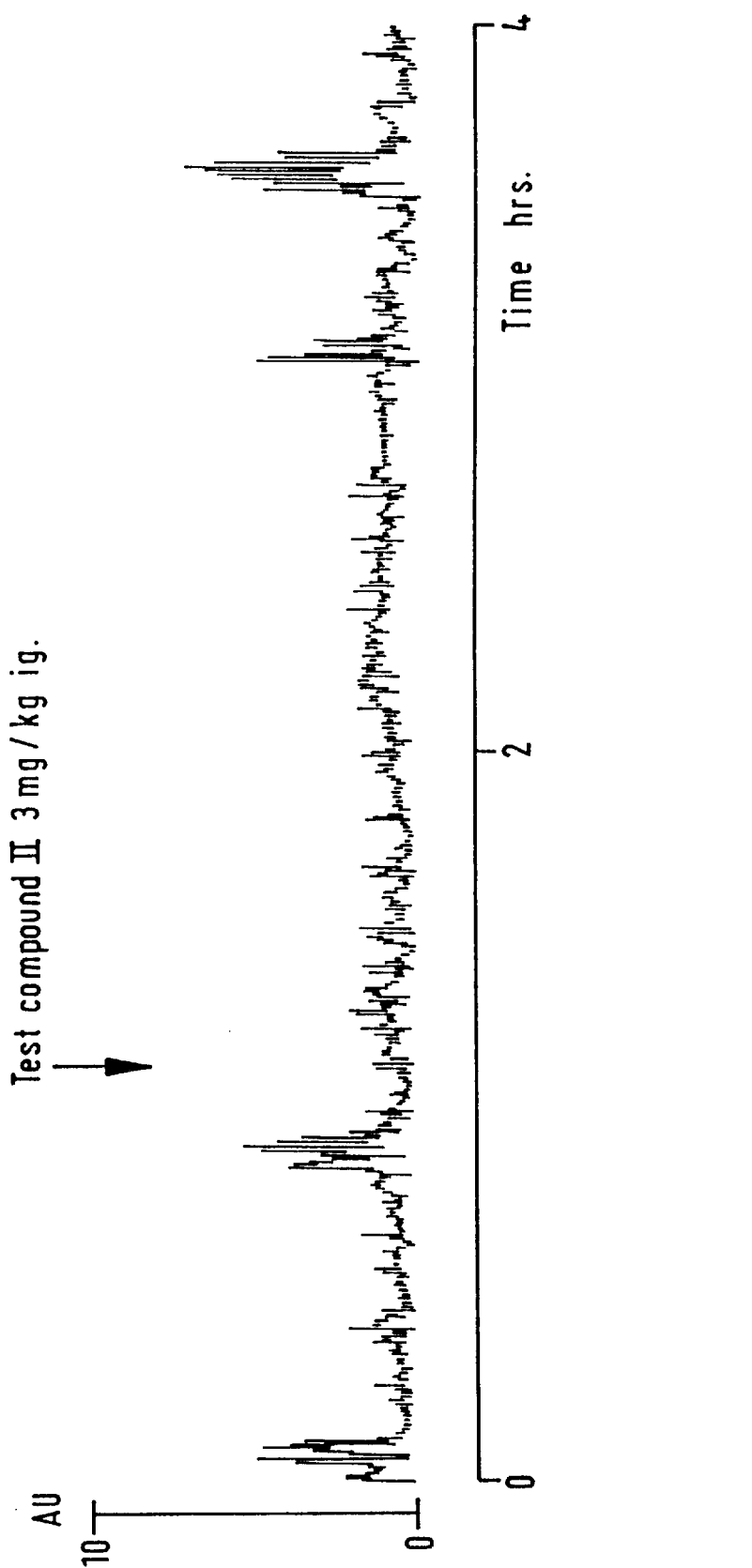

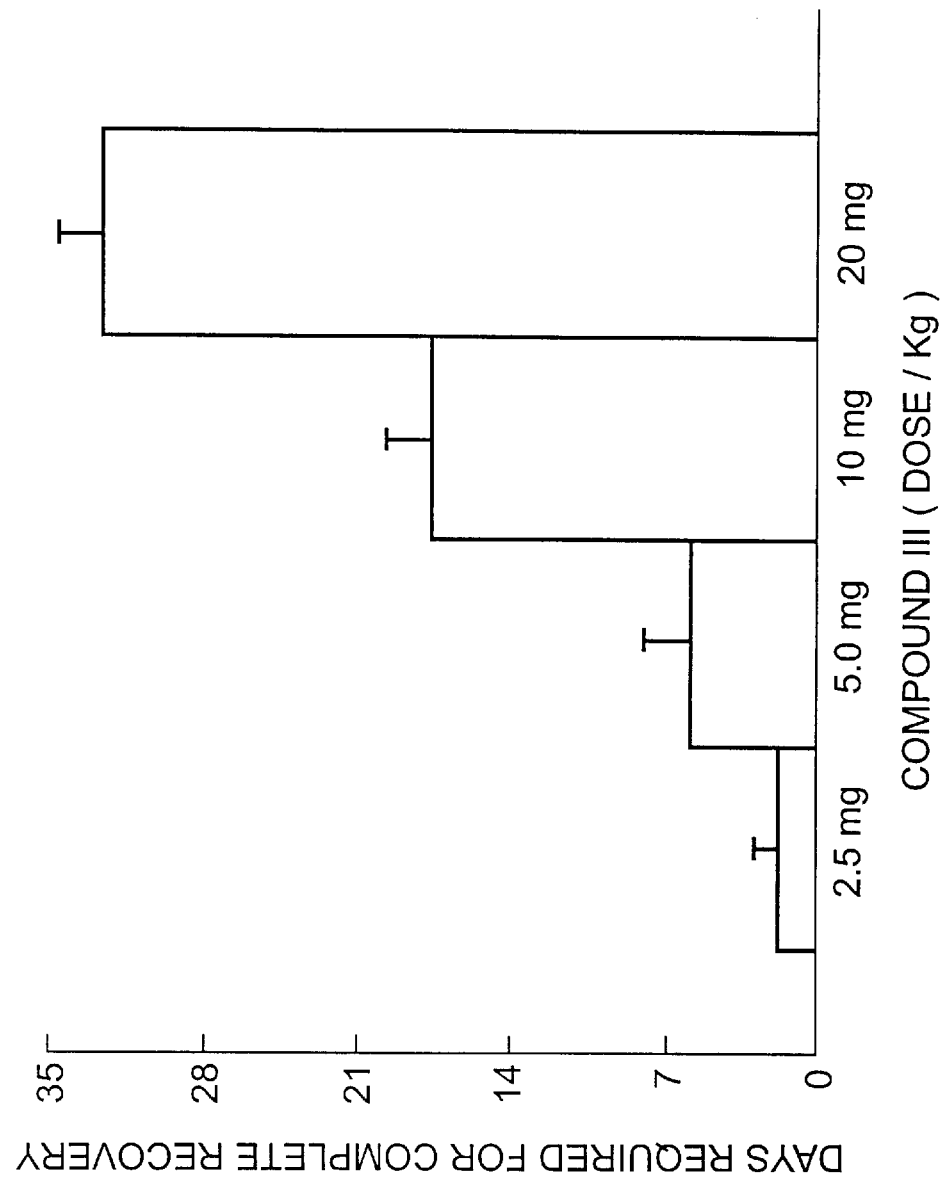

METHOD OF BLOCKING NERVE CONDUCTION BY TREATMENT WITH BRANCHED-CHAIN ESTERS OF 2-[4-(2-PIPERIDINE-ETHOXY)-BENZOYL]-BENZOIC ACID AND PHARMACEUTICALLY ACCEPTABLE SALTS THEREOF

This application is a continuation-in-part of application Ser. No. 08/232,436 filed Apr. 21, 1994, abandoned, which is a continuation of application Ser. No. 07/995,524 filed Dec. 23, 1992, abandoned, which is a continuation of application Ser. No. 07/424,338, filed Oct. 19, 1989, abandoned.

BACKGROUND OF THE INVENTION

Field of the Invention

The present invention relates to branched-chain alkyl esters of 2-[4-(2-piperidine-ethoxy)-benzoyl]-benzoic acid and pharmaceutically acceptable salts thereof, processes for their preparation, and their use as spasmolytic and anesthetic agents in medicaments.

Esters of 2-[4-(2-piperidine-ethoxy)-benzoyl]-benzoic acid of the formula I ($R_1$=lower alkyl) are described in U.S. Pat. No. 2,681,340, to be antispasmodic agents, wherein the meaning of $R_1$ as a lower alkyl group has a very limited definition. In the said definition, although $R_1$ includes lower alkyl groups, the specification only describes the preparation of straight-chain methyl, ethyl and n-butyl esters, and cites in the claims as particular compounds only the methyl and ethyl esters as the compounds of choice.

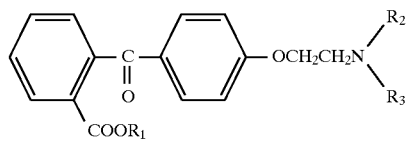

To date, no branched-chain esters of the formula I are known. Pitofenone (formula II) is a representative compound of

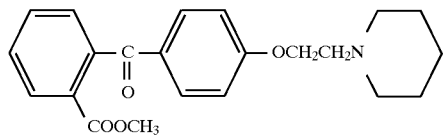

the series described in the above cited U.S. Pat. No. 2,681,340 and is used alone or in combination with metamizole in antispasmodic preparations like Baralgan®. When pitofenone is administered intravenously, it displays potent antispasmodic activity. When it is, however, administered orally, the activity is considerably reduced, which is attributed to rapid metabolism of the methyl ester to the corresponding acid.

It would be highly advantageous to have an orally active antispasmodic preparation.

The present invention describes novel branched-chain alkyl esters of 2-[4-(2-piperidine-ethoxy)-benzoyl]-benzoic acid, which are surprisingly not only more potent spasmolytic agents than pitofenone and the compounds of the class described in U.S. Pat. No. 2,681,340, but also more stable to hydrolysis by enzymes, longer acting, and metabolically more stable when administered enterally or parenterally to mammals. These properties contribute to making the compounds of the invention specially useful for medicaments that can be orally administered as spasmolytic agents.

BRIEF DESCRIPTION OF DRAWINGS

FIG. 3 shows the inhibitory effect of test compound II on colonic motility in conscious dog.

FIG. 4 shows recovery time from blocked nerve conduction using test compound II.

Figure 1:
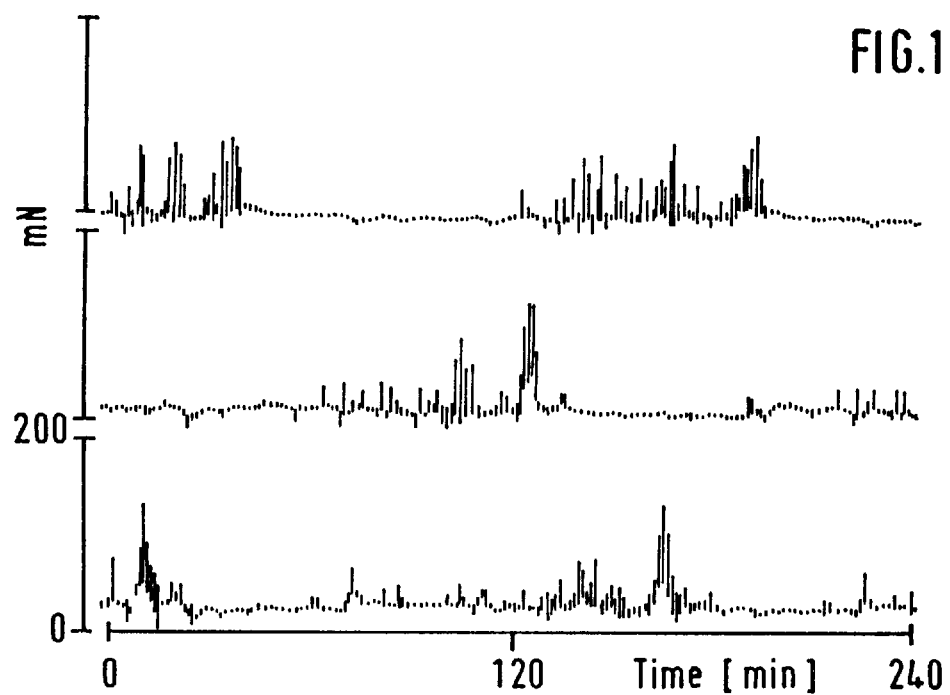
FIG. 1 shows effect of control, i.e. no drug, on small intestine motility in conscious dog.

The present invention relates to compounds represented by the general formula III, in which $R_4$ and $R_5$ may be

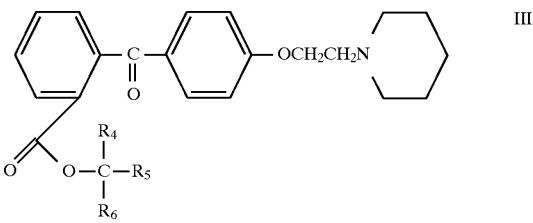

the same or different, and each of $R_4$ and $R_5$ stands for $C_1$–$C_4$ alkyl, and $R_6$ stands for hydrogen or $C_1$–$C_4$ alkyl, and their pharmaceutically acceptable salts.

$R_4$, $R_5$ and $R_6$ in the definition of $C_1$–$C_4$ alkyl may each stand for methyl, ethyl, n-propyl, isopropyl, n-butyl, isobutyl, sec-butyl and tert.-butyl; included are also all the racemates and optical isomers thereof.

The preferred meanings are for each of $R_4$ and $R_5$: $CH_3$ and $C_2H_5$, and for $R_6$: H and $CH_3$.

The particularly preferred compound of the present invention is the compound of the formula III in which $R_4$=$R_5$=$CH_3$ and $R_6$=H.

This particular compound III has prolonged nerve blocking ability which makes it an ideal therapeutic agent for the alleviation of acute and chronic pain associated with post-surgical states, neuralgias and cancer.

The invention further relates to processes for the preparation of compounds of the general formula III. Such compounds can be obtained by various methods.

A carboxylic acid of formula IV (R=H), for instance, can be derivatized at the carboxyl group by known methods [E. Haslam, Protective Groups in Organic Chemistry (J. F. W. McOmie Ed.), p.183. Plenum Press, London (1973), and E. Haslam, Tetrahedron, 1980, 36, 2409, and references cited therein], and the resulting phenolic ester of formula IV in which a is represented

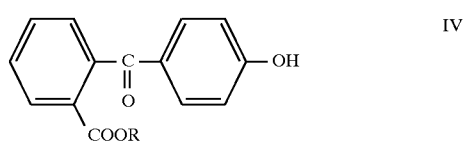

by formula V wherein $R_4$, $R_5$, $R_6$ have the definitions as

in formula III, can then be treated with a 2-piperidino ethyl derivative bearing a good leaving group, or its corresponding salt, for instance, a 2-piperidino-ethyl halide, for example, 2-piperidino-ethyl chloride or 2-piperidinoethyl chloride hydrochloride in the presence of a base to obtain the compound of the invention of formula III.

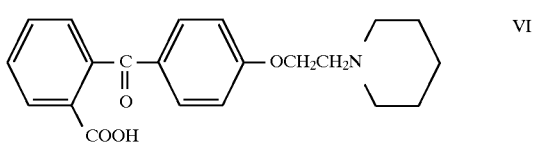

VI

Alternatively, an acid of the formula VI can directly be esterified with appropriate alcohols in presence of a condensing agent by known methods cited above.

Appropriate condensing agents are for example conc. $H_2SO_4$, trifluoroacetic anhydride and thionyl chloride.

In another method, the carboxylate salt of the acid of formula VI can be treated by known methods (loc. cit.) with appropriate alkyl halides to form compounds of formula III.

These reactions can be performed in some cases neat, or in organic solvents or mixtures thereof not interfering with the reaction, such as for example ketones, like acetone or butan-2-one, N,N-disubstituted amides, like N,N-dimethylformamide or N,N-dimethylacetamide, halogenated hydrocarbons, like carbon tetrachloride, chloroform, methylene chloride, ethers like diethyl ether, diisopropylether or methyl-tert.-butyl ether, aromatic hydrocarbons, like benzene, toluene or xylene, esters like ethyl acetate or butyl acetate, dimethylsulfoxide or hexamethyl phosphoric triamide. Also mixtures of these solvents with water can be used. When phase transfer catalysts are used, catalysts like methyltrioctylammonium chloride (for example Aliquat® 336) or tetrabutylammonium bromide are suitable.

Furthermore, under appropriate conditions, the reactant alcohol may also be used as a solvent.

The reactions can be carried out at temperatures between −20° C. and the boiling point of the solvent used.

For the conversion of compound IV, in which R is equal to formula V, to compound III, a base may be added to shorten the reaction time. As base may be considered a metal hydroxide like sodium hydroxide, potassium hydroxide, calcium hydroxide or magnesium hydroxide, a metal carbonate, like sodium carbonate or potassium carbonate, a bicarbonate, like sodium bicarbonate or potassium bicarbonate, an alcoholate like sodium methoxide or sodium ethoxide, or an organic base like tertiary amines such as triethylamine, N,N-diethylaniline or pyridine.

The compound of the invention of formula III may exist as a free base or in the form of a pharmaceutically acceptable salt with an organic or inorganic acid such as hydrochloric acid, sulfuric acid, acetic acid, malonic acid, maleic acid, tartaric acid or citric acid. Preferred is the salt with hydrochloric acid.

The compounds of the invention display the following special properties:

1) Low esterase hydrolysis rates
2) Potent and long lasting antispasmodic action in vitro and in vivo.
3) Increased bioavailability on oral administration to mammals as demonstrated in the experiments described below by using the following test compounds
4) Potent and long lasting nerve blocking, or anesthetic, effects in vitro and in vivo.

TEST COMPOUND I

Methyl-2-[4-(2-piperidino-ethoxy)-benzoyl]-benzoate hydrochloride (Pitofenone)

TEST COMPOUND II

Isopropyl-2-[4-(2-piperidino-ethoxy)-benzoyl]-benzoate hydrochloride.

TEST COMPOUND III

2-[4-(2-piperidino-ethoxy)-benzoyl]-benzoic acid.

EXPERIMENT 1

Enzymatic Hydrolysis Rates for Test Compounds:

Porcine liver esterase (0.5 U=2 μg) was preincubated in 40 mM Tris-HCl buffer, pH 8.0, at 37° C. for 5 min. The reaction was initiated with the addition of the test compound (final concentration, 1 mM) in the final volume of 250 μl. Enzyme reaction was terminated at different time intervals by the addition of 60 μl of 1M acetic acid. The solution was made alkaline (pH 10.5) by adding 0.4M NaOH and the alkaline solution was rapidly extracted (three times) with 2.5 ml of chloroform. An aliquot of the aqueous supernatant was diluted with double distilled water and the absorbance was measured at 290 nm. Amount of test compound III (molar extinction=14,400) formed was calculated. Results are shown in Table I.

TABLE I

| Time | μmol test compound III formed per mg protein per ml Test Compound | |
|---|---|---|
| (hours) | I | II |
| 0.0 | 0.00 | 0.00 |
| 0.5 | 0.50 | 0.05 |
| 2.0 | 1.62 | 0.10 |
| 3.5 | 2.78 | 0.10 |

EXPERIMENT 2

Antispasmodic Activity in Isolated Guinea Pig Ileum Model:

Small intestines obtained from freshly sacrificed guinea pigs (weight range, 200–400 g) of either sex were cleaned and stored in tyrode solution. A piece of ileum was mounted in an organ bath containing tyrode solution at 37° C. and maintained at a tension of 0.5 to 1.0 g. The solution was continuously aerated with compressed air. After an initial equilibration period, a sub-maximal dose of acetylcholine required for measurable contraction was standardized. Tension changes were monitored using an isotonic strain gauge attached to the tissue and the responses were recorded on a strip chart recorder.

Antispasmodic activity of test compounds at different concentrations was followed and the $IC_{50}$, values were calculated from dose response curves. Results are shown in Table 2.

TABLE 2

| | | Guinea pig ileum | |
|---|---|---|---|
| Test Compound | R Group | $IC_{50}$ (μg/ml) | Duration of action (min) |
| I | —$CH_3$ | 1.00 | <1.5 |
| II | —$CH(CH_3)_2$ | 0.01 | >7.0 |

EXPERIMENT 3

Antispasmodic Activity in Anaesthetized Dog

Method:

Male mongrel dogs of weight range 10 to 15 kg were anaesthetized with pentobarbitone sodium (35 mg/kg, i.v.). Slow i.v. infusion of pentobarbitone (5 mg/kg/hour) was given for maintenance anaesthesia. The endotracheal tube was inserted to facilitate spontaneous breathing. Both femoral artery and vein were cannulated respectively for recording blood pressure and administering drugs. After laparotomy, a small portion of small intestine distal to duodenum was isolated and saline filled balloon inserted and the opening was sutured. A fine polyethylene cannula was then inserted into the mesenteric artery which supplies to the area of intestine containing balloon for injection of carbachol or acetylcholine. A Statham pressure transducer was then attached to balloon cannula for recording both circular and longitudinal muscle contractions. All the parameters were recorded on 4 channel Nihon-Kohden recorder. The intestinal contractions were recorded after administering a standard dose of carbachol or acetylcholine (0.5 to 3 $\mu$g).

20 mg/kg intra-duodenally and spaIntra-duodenal administration:

Test compounds I and II were given at different doses 3,10 and smolytic activity was assessed at various time intervals.

Anti-spasmodic activity was assessed by calculating percent reduction in agonist induced contractions and also noting onset and duration of activity. The test compounds were dissolved in distilled water (1% soln.). Results see Table 3.

TABLE 3

Spasmolytic activity after intra-duodenal administration in anaesthetized dog:

| Test compounds | Dose mg/kg | Percent inhibition | On-set (min) | Duration (min) |
|---|---|---|---|---|
| Test compd. II | 3 | 54 | 7 | 35 |
|  | 10 | 83 | 6.5 | 78 |
| Test compd. I | 10 | N.A. | N.A. | N.A. |
|  | 20 | 63 | 20 | 40 |

N.A. Not active.

Intravenous Administration:

Test compounds I and II were given at different doses (10, 30, 100, 300 and 1000 $\mu$g/kg) intravenously and spasmolytic activity was assessed at different time intervals.

Anti-spasmodic activity was assessed by calculating percent reduction in agonist induced contractions. The $ID_{50}$ value was dose response curve. Results see Table 4.

TABLE 4

Spasmolytic activity after intravenous administration in anaesthetized dog:

| Test compounds | $ID_{50}$ (mg/kg, i.v.) | Duration of action (min) |
|---|---|---|
| Test compd. I | 0.140 | 10–30 |
| Test compd. II | 0.010 | >60 |

EXPERIMENT 4

Method:

Ref.: J. M. A. Zwagemakers and V. Claassen, Arzneim-Forsch/Drug Res. 30 (II) Nr.9, p.1517 (1980).

The test compounds I and II were given orally by gavage in a range of 10 to 100 mg/kg doses 30 min before charcoal suspension (0.2 ml/animal, 10% charcoal in 5% gum acacia) in 18 hrs fasted mice (male or female, weight range 18 to 25 g). 30 min after administration of charcoal animals were killed and the extent of charcoal propulsion in the small intestine was measured. The inhibitory activity of test compound on charcoal transport was assessed as percent inhibition compared to length of intestine. For control group 10 ml/kg of saline was given. Results Table 5.

TABLE 5

Effect on gastrointestinal propulsion in mice:

| Test compds | Dose mg/kg. p.o | Percent Inhibition | No. of animals |
|---|---|---|---|
| Control | 10 ml/kg (vehicle) | 12.7 ± 1.2 | 40 |
| Test compd. II | 10 | 38.0 ± 4.0 | 20 |
|  | 30 | 41.0 ± 3.0* | 20 |
|  | 60 | 46.0 ± 5.0* | 20 |
| Test compd. I | 60 | 24.0 ± 3.0 | 16 |
|  | 100 | 30.0 ± 4.3 | 13 |

*P = <0.001 compared with 60 mg/kg of pitofenone (unpaired 't' test)

EXAMPLE 5

Effects of Test Compound II (isopropyl-2-[4-(2-piperidino-ethoxy)-benzoyly-benzoate hydrochloride) on the Motility of the Small Intestine in the Conscious Dog Methods:

Male dogs (THG Tierhandelsgesellschaft Rodenbach, Hoe: BEAK (Beagle)) weighing 15–20 kg were used in all experiments. At least 4 weeks prior to the experiment the dogs had been equipped with miniaturized strain gage force transducers (T1–T3) (2×4 mm), sutured onto the gut at the locations mentioned below. The cables of the transducers were embedded into a cannula which carried the plug for external electric connection. This stainless steel cannula was implanted into the abdominal wall, close below the costal arch. Each transducer was connected to a measuring bridge. The signals were on line stored using a HP 9835 A computer, allowing later analysis of the data.

T1: Proximal jejunum

T2: Distal jejunum

T3: Ileum 18 hours prior to the experiment food was withdrawn from the animals, water ad libitum. All experiments started between 08:00 and 09:00 am.

The following motility parameters were determined:

The integral under the concentration curves at 10 min intervals (mN×10min) as an index of phase I+II activity. The duration of drug action (min.)

The duration of the interdigestive migrating complex (IMC) (min) as a measure of phase III activity.

Treatments:

Test Compound II was given at doses of 0.2 and 0.5 mg/kg i.v. or 5 mg/kg i.g., dissolved in saline, in a volume of 1 ml/kg (i.v.) or 2 ml/kg (i.g.), n=3–6. Control n=26.

Reference substances: Buscopan, pitofenon.

Buscopan was given at doses of 0.3 and 1 mg/kg i.v., dissolved in saline, in a volume of 1 ml/kg, n=4–6. Pitofenone was given at doses of 1 mg/kg i.v., dissolved in saline, in a volume of 1 ml/kg, n=8.

Statistical methods:

$1D_{50}$-values were determined graphically.

Results: Tables 6–8, FIGS. 1–2.

Summary:

All three compounds inhibited the spontaneous motility of the small intestine in the conscious dog (Tables 6–7). The rank order of potency was:

Test Compound II>buscopan>pitofenon

The intravenous $IC_{50}$-values determined from maximal inhibition (Table 7) were:

Test Compound II: 220 µg/kg

Buscopan: 600 µg/kg

Pitofenon: 1000 µg/kg

The inhibitory effect of an i.v.-injection of 0.5 mg/kg of test compound II lasted for approximately one hour, whereas buscopan at a dose of 1 mg/kg i.v. had only a duration of action of 30 min (Table 6).

Figure 2:
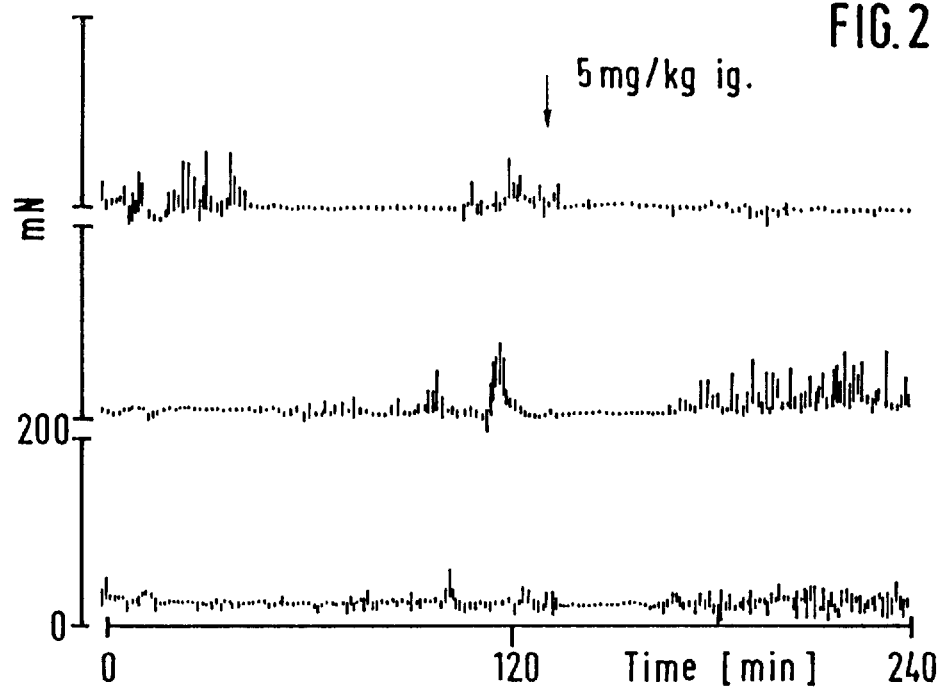
FIG. 2 shows effect of test compound II on small intestine motility in conscious dog.

When test compound II was given intragastrically, 5 mg/kg, a pronounced inhibition of phase III activity could be monitored (Table 8, FIG. 1,2).

TABLE 8

Effect on small intestinal moitility in the conscious dog (Phase III activity) Intragastrical application

| Treatment | Dose mg/kg | N | Duration of cycles min |
|---|---|---|---|
| Control | — | 26 | 121 ± 7 |
| Test compound II | 5 | 3 | 298 ± 18* |

Results show means ± SD
*p <0.05 vs. control

EXPERIMENT 6

Effects on the Motility of the Large Bowel in Conscious Dogs

Methods:

Male dogs (THG Tierhandelsgesellschaft Rodenbach, Hoe:BEAK (Beagle)) weighing 15–20 kg were used in all experiments.

At least 4 weeks prior the experiment the dogs had been equipped with miniaturized strain gage force transducers (T1–T2) (2×4 mm), sutured onto the gut at the locations mentioned below. The cables of the transducers were

TABLE 6

Effect of small intestinal motility (Phase I and II activity)
(Area under the contraction curve in mN x 10 min as a measure for gut motility for phase I and II)

| | Dose | | Predrug | Postdrug mN x 10 min | | | | | |
|---|---|---|---|---|---|---|---|---|---|
| | mg/kg | N | −20–0 | 10 | 20 | 30 | 40 | 50 | 60 min |
| Test compound II | 0.2 | 4 | 2.15 ± 0.70 | 1.54 ± 0.36 | 1.42 ± 0.52 | 1.88 ± 1.04 | 1.77 ± 0.86 | 1.78 ± 0.68 | 2.19 ± 1.13 |
| | 0.5 | 6 | 2.62 ± 1.39 | 0.54 ± 0.69 | 0.50 ± 0.57 | 0.99 ± 0.80 | 1.17 ± 0.73 | 1.61 ± 1.16 | 2.46 ± 2.23 |
| Pitofenon | 1 | 8 | 2.96 ± 2.0 | 1.58 ± 1.84 | 2.01 ± 1.45 | 2.59 ± 1.59 | 2.29 ± 1.92 | 3.16 ± 1.12 | 3.64 ± 2.42 |
| Buscopan | 0.3 | 6 | 2.09 ± 0.81 | 1.78 ± 0.86 | 1.74 ± 1.28 | 2.17 ± 0.98 | 2.15 ± 0.69 | 1.80 ± 0.67 | 1.60 ± 0.82 |
| | 1 | 4 | 2.03 ± 0.49 | 0.85 ± 0.57 | 0.86 ± 0.53 | 1.23 ± 0.21 | 2.03 ± 1.10 | 2.09 ± 0.89 | 1.99 ± 0.70 |

Results show means ± SD

TABLE 7

Effect on small intestinal motility in the conscious dog
(Phase I + II activity) i.v. (Area under the concentration curve in mN · 10 min as a measure for gut motility for phase I and II)

| | | Inhibition | | Duration a) | |
|---|---|---|---|---|---|
| Treatment | Dose mg/kg | Maximal % | Mean | of action min | $1D_{50}$ mg/kg |
| Test compound II | 0.2 | 34 | 22 ± 4 | 50 | 0.26 |
| | 0.5 | 81 | 54 ± 11 | 60 | |
| Pitofenon | 1 | 47 | 29 ± 7 | 40 | 1 |
| Buscopan | 0.3 | 29 | 23 ± 6 | 20 | 0.6 |
| | 1 | 58 | 52 ± 6 | 30 | |

Results show means ± SD
a) = when postdrug values reached 90% or more of predrug values embedded into a cannula which carried the plug for external electric connection. This stainless steel cannula was implanted into the abdominal wall, close below the costal arch. Each transducer was connected to a measuring bridge. The signals were on-line stored using a HP 9835 A computer, thereby allowing later analysis of the data.

T1: Colon ascendens 10 cm aboralfrom the ileoceval valve (ICV)

T2: Colon transversum 25 cm aboard from the ICV 18 hours prior to the experiment food was withdrawn from the animals, water ad libidum All experiments started between 08:00 and 09:00 am.

The following parameters were determined:

The duration of the cycle (min)

The duration of the colonic motor complex (CMC) (min)

The maximal height of the concentrations (AU: arbitrary units)

Data from the two recording sites (T1–T2) were pooled.

Treatments:

Test compound II was given at a dose of 3 mg/kg i.g., dissolved in saline, in a volume of 2 ml/kg, n=5, control n=23.

Statistical methods: For detection of significant differences (p<0.05) the unpaired t-test was used. Only significant differences were indicated by *.

Results: Table 9, FIG. 3

TABLE 9

Effects on the colonic motor complex (CMC) of the large bowel in the conscious dog.
Route of administration: intragastrically

| Treatment | Dose mg/kg | $N^a$ | $N^b$ | Duration Cycle min | CMC min | Max. height of CMC AU | Total number of spikes n/CMC |
|---|---|---|---|---|---|---|---|
| Control | — | 28 | 112 | 39 ± 10 | 10 ± 3 | 50 ± 25 | 5.5 ± 1.7 |
| Test compound | 1 | 4 | 4 | 28 ± 11 | 6 ± 2 | 50 ± 25 | 5.6 ± 1.7 |
| II | 3 | 14 | 14 | 136 ± 42* | 11 ± 3 | 40 ± 23 | 5.5 ± 1.0 |
| Buscopan | 3 | 6 | 6 | 35 ± 19 | 6 ± 4 | 35 ± 17 | ND |
|  | 10 | 4 | 4 | 32 ± 5 | 5 ± 1 | 35 ± 10 | ND | a: Number of experiments
b: Number of cycles analysed
ND: not determined

Summary:

Test compound II, 4 mg/kg i.g., inhibited colonic motility (CMC in the conscious dog completely for about 2 hours. 1 mg/kg i.g. was uneffective. Buscopan at doses of 3 and 10 mg/kg i.g. had no effect on colonic motility in the conscious dog.

EXPERIMENT 7

Conduction block anaesthesia was produced in the rat using compound II [(Isopropyl 2-(4-2-piperidinoethoxy)-benzoyl)benzoate hydrochloride] according to the method of Traunt. (Traunt, A. P. Arch. Int. Phamacodyn. 115:483–497, 1957).

Compound II produced a dose-dependent blockade of nerve conduction when injected near the sciatic nerve in the rat. The conduction block produced was of long duration and required a number of days for complete recovery. The time taken for recovery was dose-dependent as shown in the FIG. 4. A dose of 20 mg/kg compound II blocked nerve conduction in the rat for about 33 days. Ten mg/kg of compound II blocked the nerve for 18±2 days (n=25). In comparison, 10 mg/kg of lignocaine, a standard local anesthetic, produced conduction block for only 0.086±0.01 days (n-10). Thus, it can be concluded that the compound II can produce a reversible blockade of nerve conduction lasting for hours to days depending on the dose employed. This long lasting but reversible blockade of nerve conduction is of significant interest in the treatment of cancers, neuralgias and post-surgical states.

The compounds of the invention and their salts possess valuable spasmolytic properties and are suitable for the treatment of all types of spasms, mild and acute They also possess prolonged nerve blocking ability and are suitable for treatment of pain associated with cancer, neuralgias and post-surgical states. The compounds of this invention and their salts can also be used in combination with other pharmacologically active substances, for example, antiinflammatory, analgesic, anti-anxiety, CNS depressant agents and other such therapeutic agents that are pharmacologically acceptable to be used in combination with spasmolytic and anaesthetic agents.

The compounds of the invention and their physiologically tolerable salts can be administered orally, parenterally, (intramuscularly, intravenously, subcutaneously) rectally, or topically, optionally in the form of an aerosol. When used as a nerve blocking agent, they are administered by injection.

The compounds of the invention and their physiologically tolerable salts can be administered either per se or in admixture or conjunction with a pharmaceutically suitable carrier material. For oral administration the active compounds may be admixed with the carrier and transformed into the usual form for administration, for example, tablets, push-fit capsules, aqueous alcoholic or oily suspensions or solutions. Suitable carrier materials are, for example, magnesium carbonate, milk sugars maize starch and magnesium stearate. The compositions can be prepared in the form of dry or moist granules. Any oily carrier or solvents may be a vegetable or animal oil, for example, sunflower oil or cold-liver oil.

The active compounds may be administered intravenously. To this end, a compound of the invention or a physiologically tolerable salt thereof, as far as it has sufficient solubility, is generally dissolved in one of the usual auxiliaries, which may also act as a dissolving intermediary or buffer.

The solvents for intravenous administration are, for example, water, physiological sodium chloride solution and dilute alcohols, for example, ethanol, propanediol and glycerol; furthermore, sugar solutions, for example, glucose and mannitol solutions, or a mixture of two or more of the aforesaid solvents.

The pharmaceutical preparations are preferably in unit dosage form. When used as a nerve blocker, the dosage and density schedule will depend on the desired duration of action with a range from hours to days.

The following examples illustrate the invention but do not restrict the scope of the invention.

EXAMPLE I

Isopropyl-2-[4-(2-piperidino-ethoxy)-benzoyl]-benzoate

Method I

To 2-(4-hydroxy-benzoyl)-benzoic acid (60 g, 0.25 mol) were added 2-propanol (1020 ml) and concentrated $H_2SO_4$ (25 ml) and the reaction mixture was refluxed for 24 hours. 2-Propanol then was distilled off under vacuum. The residue was dissolved in ethyl acetate (1000 ml), cooled and washed with sodium bicarbonate solution (2×500 ml~ followed by water (750 ml), dried and concentrated to give 70 g of isopropyl ester as a dark oil, which could be crystallized from diisopropyl ether to give white crystals, mp. 95°–97° C.

A mixture of the isopropyl ester (28.4 g, 0.1 mol), 2-piperidinoethyl chloride (23.6 g, 0.16 mol) and anhydrous $K_2CO_3$ (57 g, 0.38 mol) in dry 2-butanone (1000 ml) was refluxed for 6 hours. The solvent was distilled off under vacuum, the mixture poured into water (800 ml) and extracted with ethyl acetate (1.1 lit). The ethyl acetate layer was washed with 1% aqueous KOH solution, followed by water (2×500 ml), dried over anhydrous $Na_2SO_4$ and concentrated to give 36 g of a dark viscous oil. Flash chromatography (silica gel, $CHCl_3$-EtOAc-$CH_3OH$, 74:20:6) gave 33 g (83%) of the title compound as a viscous oil, which could be crystallized from n-pentane at ca. −6° C. to give white crystals, mp 34°–35° C.

Alternatively a mixture of the isopropylester (28.4 g, 0.1 mole), 2-piperidinoethyl chloride hydrochloride (25.9 g, 0.14 mole), anhydrous $K_2CO_3$ (38.7 g, 0.28 mole) in 2-butanone (215 ml) containing water (9.5 ml) was refluxed for 3 hours. After workup as described above, 34.5 g of the title compound were obtained in 87% yield.

IR (neat): 3000, 2950, 1720, 1670, 1600 cm$^{-1}$, NMR (CdCl$_3$): δ 7.92–8.02 (m, 1H), 7.19–7.7 (m, 5H) 6.72–6.92 (m, 2H), 4.96 (h, 1H, 5.8Hz), 4.12 (t, 2H, 6.5 Hz), 2.78 (t, 2H, 6.5Hz), 2.40–2.60 (m, 4H), 1.40–1.75 (m, 6H), 1.06 (d, 6H, 5.8 Hz)

METHOD II

A mixture of 2-[4-(2-piperidino-ethoxy)-benzoyl]-benzoic acid (14.8 g, 0.04 mol), dry 2-propanol (300 ml) and 14.8 ml concentrated H$_2$SO$_4$ was refluxed for 9 hours. 2-propanol was distilled off in vacuo. Aqueous potassium carbonate was added to the cooled reaction mixture and it was extracted with ether (3×200 ml).

The ether layer was washed with water, dried and concentrated to give 10.8 g 6f an oil. Flash chromatography (silica gel, CHCl$_3$- EtOAc-CH$_3$OH, 74:20:6) gave 6.7 g (41%) of the title compound as a viscous oil, identical in its physical properties with product of example 1, method I.

METHOD III

2-[4-(2-Piperidino-ethoxy)-benzoyl]-benzoic acid (23.4 g, 0.07 mol) was suspended in 2-propanol (400 ml) at −5° C. Thionyl chloride (67 ml) was added dropwise over a thirty minute period maintaining the temperature between −5° to −10° C. The clear solution was refluxed for 4.5 hours and cooled. Thionyl chloride and 2-propanol were distilled off under vacuum. To the reaction mixture was added a saturated solution of NaHCO$_3$ until the pH reached 8 and the mixture extracted with ether (250 ml×3). The ether layer was washed with water (200 ml×2), brine (200 ml×2), dried over anhydrous Na$_2$SO$_4$ and concentrated to give 21.4 g of a crude oil. Flash chromatography (silica gel, CHCl$_3$-EtOAc-MeOH) gave 12.1 g (46%) of the title compound as a viscous oil identical in its physical properties with product of Example 1, Method I.

METHOD IV

A mixture of 2-[4-(2-piperidino-ethoxy)-benzoyl]-benzoic acid (1.05 g, 0.003 mol), 20 ml HMPA and a solution of NaOH (0.18 g, 0.0045 mol) in 1.5 ml water was stirred for 30 min and 2-bromopropane (1.22 ml, 0.012 mol) was added. The reaction mixture was stirred at room temperature for 24 hours It was then poured into water (150 ml) and extracted with ethyl acetate. The ethyl acetate layer was washed several times with waters dried over anhydrous Na$_2$SO$_4$ and concentrated in vacuo to give 1.3 g of a viscous oil. Flash chromatography (silica gel, CHCl$_3$-CH$_3$OH) gave 0.72 g (62%) of the title compound as an oil, identical in its physical properties with product of example 1, Method I.

METHOD V

To a mixture of 2-bromopropane (0.62 g, 5 mmol) and Aliquat 336 (0.22 g, 0.54 mmol) was added dry powdered potassium salt of 2-[4-(2-piperidino-ethoxy)-benzoyl]-benzoic acid (2.15 g, 5.4 mmol). The flask was fitted with a CaCl$_2$ guard tube and shaken for 15 mins. It was then filtered with a reflux condenser and the reaction mixture heated at 60° C. (bath temperature) for 25 hours. The product was triturated with 25% EtOAc-petroleum ether (25 ml) and filtered over a bed of neutral alumina (40 g, grade I) followed by elution with 25% EtOAc-petroleum ether (150 ml). The combined filtrate was concentrated to give 1.5 g (75 %) of the title compound as a colourless viscous oil, identical in its physical properties with product of Example 1, Method I.

EXAMPLE 2

Isopropyl-2-[4-(2-piperidino-ethoxy)-benzoyl]-benzoate hydrochloride 5.54 g of isopropyl-2-[4-(2-piperidino-ethoxy)-benzoyl]-benzoate was dissolved in 40 ml dry CH$_2$Cl$_2$. Ethereal HCl was added dropwise until the pH was between 2 and 3. Excess HCl was removed on a steam bath. The solvent was distilled off in vacuo to give a sticky brown residue which was crystallized from EtOH-Et$_2$O. The resulting white crystals of the title compound were filtered and washed with 2% EtOH-Et$_2$O.

Yield: 3.31 g (58%)

mp 110°–112° C.; Anal. Calcd. for C$_{24}$H$_{30}$ClNO$_4$: C, 65.37; H, 7.09; N, 3.18; Cl, 8.04. Found: C, 65.62; H, 7.13; N, 3.16; Cl, 8.38.

It is claimed:

1. A method of blocking nerve conduction comprising administration of an effective amount of a compound of the formula III

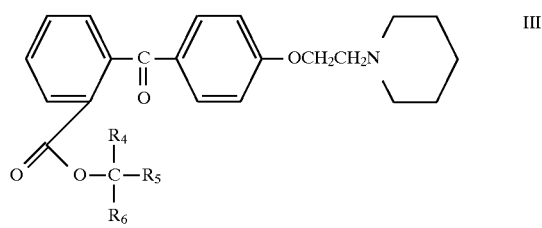

wherein R$_4$ and R$_5$ stands for CH$_3$ and R$_6$ stands for hydrogen, which compound is isopropyl-2-[4-(2-piperidino-ethoxy)-benzoyl]-benzoate.

2. A method for the treatment of acute and chronic pain comprising administration of an effective amount of a compound of the formula III

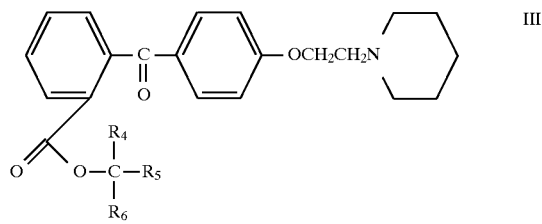

wherein R$_4$ and R$_5$ stands for CH$_3$ and R$_6$ stands for hydrogen, which compound is isopropyl-2-[4-(2-piperidino-ethoxy)-benzoyl]-benzoate.

* * * * *